United States Patent [19]

Wright

[11] 4,091,011

[45] * May 23, 1978

[54] 3-CYANO-OXANILIC ACID DERIVATIVES

[75] Inventor: John B. Wright, Kalamazoo, Mich.

[73] Assignee: The Upjohn Company, Kalamazoo, Mich.

[*] Notice: The portion of the term of this patent subsequent to Oct. 19, 1993, has been disclaimed.

[21] Appl. No.: 744,692

[22] Filed: Nov. 24, 1976

Related U.S. Application Data

[62] Division of Ser. No. 477,815, Jun. 10, 1974, abandoned.

[51] Int. Cl.² .................................. C07C 121/78
[52] U.S. Cl. .............................. 260/465 D; 424/304
[58] Field of Search ............................. 260/465 D

[56] References Cited

U.S. PATENT DOCUMENTS 3,966,965  6/1976  Sellstedt et al. .................. 424/317
3,987,192  10/1976  Wright .............................. 424/304

FOREIGN PATENT DOCUMENTS 994,714  6/1964  United Kingdom.

Primary Examiner—Dolph H. Torrence
Attorney, Agent, or Firm—Martin B. Barancik

[57] ABSTRACT

It has now been discovered that compounds of FIG. 1

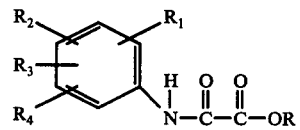

are useful in the prophylactic treatment of sensitized humans and animals for allergy and all anaphylactic reactions of a reagin or non-reagin mediated nature. The compounds are formulated with pharmaceutical carriers for oral, parenteral, inhalation, or rectal means of administration. Certain compounds are novel.

7 Claims, No Drawings

3-CYANO-OXANILIC ACID DERIVATIVES

CROSS-REFERENCE TO RELATED APPLICATIONS

This application is a divisional of copending application Ser. No. 477,815, filed June 10, 1974 and now abandoned.

BRIEF SUMMARY OF THE INVENTION

It has now been discovered that compounds of FIG. 1 are useful in the prophylactic treatment of sensitized humans and animals for allergy and all anaphylactic reactions of a reagin or non-reagin mediated nature. The compounds are formulated with pharmaceutical carriers for oral, parenteral, inhalation, or rectal means of administration. Certain compounds are novel.

DETAILED DESCRIPTION OF THE INVENTION

In accordance with the invention, pharmaceutical compositions are provided wherein in association with a pharmaceutical carrier are compounds of FIG. 1, hereafter referred to as Group A,

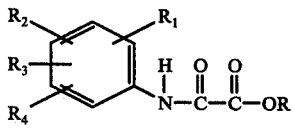

(I)

wherein R is selected from the group consisting of hydrogen, a physiologically acceptable metal or amine cation, alkyl of one to twelve carbon atoms, inclusive, cycloalkyl of five to six carbon atoms, inclusive,

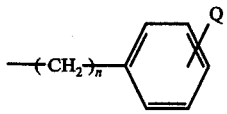

wherein $n$ is an integer of zero to three, inclusive, and Q is selected from the group consisting of hydrogen, alkyl of one to six carbon atoms, fluoro, chloro, and bromo; $R_1$, $R_2$, $R_3$ and $R_4$ are the same or different and are selected from the group consisting of hydrogen, cyano which is not ortho to the $$-\underset{H}{N}-\underset{\|}{\overset{O}{C}}-\underset{\|}{\overset{O}{C}}-OR$$

group, amino, nitro, fluoro, chloro, bromo, trifluoromethyl, alkyl of one to four carbon atoms, inclusive, alkoxy of one to four carbon atoms, inclusive,

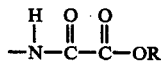

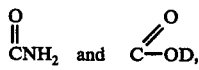

wherein D is selected from the group consisting of hydrogen, alkyl of one to four carbon atoms, inclusive, and a physiologically acceptable metal or amine cation, with the proviso that when D is hydrogen or a physiologically acceptable metal or amine cation, R is the same as D.

A further aspect of the invention are compositions with compounds of Group A wherein $R_1$ is hydrogen.

Another aspect of the invention are compositions with compounds of Group A wherein $R_1$ and $R_2$ are hydrogen.

A still further aspect of the invention are compositions with compounds of Group A wherein $R_1$, $R_2$ and $R_3$ are hydrogen.

A further aspect of the invention are compositions with compounds, hereafter referred to as Group B, of Group A wherein $R_1$, $R_2$, $R_3$ and $R_4$ are the same or different and are selected from the group consisting of hydrogen, cyano which is not ortho to the $$-\underset{H}{N}-\underset{\|}{\overset{O}{C}}-\underset{\|}{\overset{O}{C}}-OR$$

group, fluoro, chloro, trifluoromethyl, alkyl of one to three carbon atoms, inclusive, alkoxy of one to three carbon atoms, inclusive, and

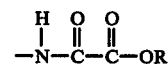

wherein D is defined as in Group A.

Another aspect of the invention are compositions with compounds of Group B wherein $R_1$ is hydrogen.

A still further aspect of this invention are compositions with compounds of Group B wherein $R_1$ and $R_2$ are hydrogen.

Another aspect of the invention are compositions with compounds of Group B wherein $R_1$, $R_2$ and $R_3$ are hydrogen.

A still further aspect of the invention are compositions with compounds, hereafter referred to as Group C, of Group A wherein $R_1$, $R_2$, $R_3$ and $R_4$ are the same or different and are selected from the group consisting of hydrogen, alkyl of one to three carbon atoms, inclusive, alkoxy of one to three carbon atoms, inclusive, fluoro, chloro, and trifluoromethyl.

A further aspect of this invention are compositions of compounds of Group C wherein $R_1$ is hydrogen.

Another aspect of the invention are compositions of compounds of Group C wherein $R_1$ and $R_2$ are hydrogen.

A further aspect of the invention are compositions of compounds of Group C wherein $R_1$, $R_2$ and $R_3$ are hydrogen.

Preferred R group substituents for each of the groups and subgroups disclosed above are hydrogen, a physiologically acceptable metal or amine cation, alkyl of one to six carbon atoms, inclusive, phenyl, benzyl, and phenethyl.

Further R group substituent groups are hydrogen and a physiologically acceptable metal or amine cation.

As employed throughout the specification and the claims, the phrase "alkyl of one to 12 carbon atoms, inclusive" includes methyl, ethyl, propyl, butyl, pentyl, hexyl, heptyl, octyl, nonyl, decyl, undecyl, dodecyl and isomers thereof. Illustrative examples of the isomers are isopropyl, tert. butyl, neopentyl, 2,3-dimethylbutyl, isoheptyl, 2,2,4-trimethyloctyl, 3-propyl-4-methylpentyl, isodecyl, isoundecyl and isododecyl. When alkyl is limited to a lesser number of carbon atoms, the scoping is intended within that number of carbon atoms. The phrase "a physiologically acceptable metal or amine cation" is that metal or amine which is accepted in an essentially non-toxic manner by a mammal. Illustrative examples of such metals are the alkali metals, e.g., lithium, sodium, and potassium, and the alkaline earth metals, e.g., magnesium and calcium. Other metals, e.g., aluminum, zinc, and iron are also within the scope of this invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,5-dimethylpiperazine, 2-methylpiperidine, and the like, as well as amines containing water-solubilizing or hydrophilic groups, e.g., mono-, di-, and triethyanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, glactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The compounds are prepared by methods known in the art. For example, methods outlined in U.S. Pat. No. 3,639,249, Column 3, Line 38, to Column 5, line 18, can be used with facility. Also see the preparatory sections of U.S. Ser. No. 382,762. Starting materials are readily prepared from literature references.

Illustrative compounds which can be compounded into the compositions of this invention are the following:

TABLE I

| | | R is ethyl | |
|---|---|---|---|
| $R_1$ | $R_2$ | $R_3$ | $R_4$ |
| H | H | H | H |
| H | 3-CN | H | H |
| H | 3-CN | 4-CN | H |
| H | 3-CN | 4-CN | 5-CN |
| H | 3-CN | 4-Cl | 6-$C_2H_5$ |
| H | 2-Cl | 4-$OCH_3$ | 5-$NO_2$ |
| H | 2-$NH_2$ | 3-$CF_3$ | 6-$COOCH_3$ |
| H | 2-OH | 3-$CONH_2$ | 6-$C_4H_9$ |
| 2-$CH_3$ | 3-$CH_3$ | 4-$CH_3$ | 5-$CH_3$ |
| 2-$OC_2H_5$ | 4-$C_3H_7$ | 5-CN | 6-Cl |
| H | H | H | 5-$CONH_2$ |
| H | H | H | 3-OH |
| H | H | H | 4-F |
| H | H | H | 5-i-$C_3H_7$ |
| H | H | H | 2-$C_4H_9$ |
| H | H | H | 3-Cl |
| H | H | H | 4-$CF_3$ |
| H | H | 3-$CH_3$ | 5-Oi-$C_3H_7$ |
| H | H | 2-Cl | 4-$COOC_2H_5$ |
| H | H | 5-$CF_3$ | 4-$NO_2$ |
| H | H | 3-$C_2H_5$ | 4-$C_2H_5$ |

TABLE II

The compounds of Table I are converted to the following esters:
i-butyl
2,2-dimethylbutyl
hexyl
2,2,4-trimethylpentyl
isodecyl
dodecyl
phenyl
cyclopentyl
benzyl
cyclohexyl
phenethyl
3-(phenyl)propyl
o-methylphenyl
m-ethylbenzyl
p-isobutylphenethyl
o-fluorophenyl
m-chlorobenzyl
p-bromophenethyl

TABLE III

The compounds of Table I are converted to compounds wherein R is a physiologically acceptable metal or amine cation or hydrogen by suitable methods. For example, sodium or tris(hydroxymethyl)aminomethane (THAM) salts are readily prepared.

Following are illustrative preparations of compounds of the invention which are formulated into pharmaceutical compositions.

EXAMPLE 1

2'-Chloro-5'-cyanooxanilic acid a. 3'-Amino-4'-chloro-benzonitrile

A solution of 116 gm. of stannous chloride dihydrate in 280 ml. of concentrated hydrochloric acid is stirred and 25.2 gm. (0.14 mole) of 4'-chloro-3'-nitrobenzonitrile is added. The temperature rises to 81° and is allowed to cool to room temperature over a period of 2 hours. The mixture is cooled to 0° in an ice bath and 50% sodium hydroxide is added until strongly basic.

The precipitate is removed by filtration. The precipitate is washed three times with ethyl acetate. The combined ethyl acetate extracts are shaken thoroughly with the aqueous filtrate. The phases are separated and the organic phase dried over magnesium sulfate. The drying agent is removed by filtration and the filtrate evaporated to dryness in vacuo. There is obtained 16.0 gm. of white crystalline solid that melts at 89°-92°.

b. Ethyl, 2'-chloro-5'-cyano-oxanilate

To a stirred solution of 15.5 gm. (0.101 mole) of 3'-amino-4'-chloro benzonitrile in 20 ml. of dimethylformamide is added 120 ml. of ethyl acetate and 12.22 g. (0.121 mole) of triethylamine. The solution is cooled to 0° in an ice bath and 16.52 g. (0.121 mole) of ethyl oxalylchloride added. The mixture is stirred in an ice bath for one hour and allowed to warm to room temperature overnight.

The precipitate is removed by filtration and the filtrate evaporated to an oil in vacuo. The oil is poured into 800 ml. of water, stirred for thirty minutes and the water decanted off. The residue is recrystallized from ethanol. There is obtained 13.85 gm. (54%) of cream colored needles that melt at 82°-83°.

Anal. Calcd. for: $C_{11}H_9ClN_2O_3$ C, 52.29; H, 3.59; Cl, 14.03; N, 11.09. Found: C, 52.34; H, 3.66; Cl, 14.09; N, 11.33. Infrared: (nujol mull) 3360 (NH), 2230 (C N), 1720 (C═O), 1595, 1580, 1530 (C═C/amide II) cm$^{-1}$.

c. 2'-Chloro-5'-cyanooxanilic acid

A solution of 6.32 gm. (0.025 mole) of ethyl-2'-chloro-5'-cyano-oxanilate in 100 ml. of methylene chloride is placed in a separatory funnel and there is added a solution of 25 ml. of 1 N sodium hydroxide diluted to 200 ml. with water. A precipitate forms and is removed by filtration. The precipitate is dissolved in 800 ml. of water. The aqueous solution is acidified with dilute hydrochloric acid. The precipitate is removed by filtration. There is obtained 5.46 gm. (97%) of white solid material that melts at 295° (dec.).

EXAMPLE 2

(3-Amino-2,4-dichloro-5-cyanophenyl)-oxamic acid a. 2,4-Dichloro-3,5-dinitrobenzoyl chloride A mixture of 75.0 g. (0.2669 mole) of 2,4-dichloro-3,5-dinitrobenzoic acid and 55.59 g. (0.2669 mole) of phosphorus pentachloride is heated at reflux for 90 minutes and cooled to room temperature. The phosphorus oxychloride is distilled off in vacuo. The residue is recrystallized from cyclohexane to yield 75.9 gm. (95%) of yellow needles melting at 99°-101°.

b. 2,4-Dichloro-3,5-dinitrobenzamide

A mixture of 74.9 g. (0.25 mole) of 2,4-dichloro-3,5-dinitrobenzoyl chloride and 200 ml. of concentrated ammonia is placed in a mortar and ground with a pestle for ten minutes. The mixture stands for 2 hours at room temperature. The yellow precipitate is removed by filtration and washed with water. There is obtained 67.7 gm. (97%) of yellow needles melting at 263°-265°. Recrystallization of 1.00 g. of material from ethanol yields 390 mg. of yellow needles melting at 262°-263°.

c. 2,4-Dichloro-3,5-dinitrobenzonitrile

A mixture of 66.0 gm. (0.235 mole) of 2,4-dichloro-3,5-dinitrobenzamide and 140 ml. of phosphorus oxychloride is heated at reflux for 1 hour. The solution is cooled to room temperature. The excess phosphorus oxychloride is distilled off in vacuo. The solid residue is triturated with ice-water and filtered. There is obtained 54.0 g. (88%) of a tan solid melting at 139°-141°.

d. 2,4-Dichloro-3,5-diaminobenzonitrile

A solution of 330 g. (1.46 mole) of stannous chloride dihydrate in 807 ml. of concentrated hydrochloric acid is stirred and there is added 53.5 gm. (0.204 mole) of 2,4-dichloro-3,5-dinitrobenzonitrile. The temperature rises to 85° and is then allowed to cool to room temperature over a period of 2 hours. The mixture is cooled to 5° in an ice-bath and there is added, slowly, 50% sodium hydroxide until the mixture is strongly basic. The precipitate is removed by filtration. The filtrate is placed in a separatory funnel. The precipitate is extracted with three volumes of ethyl acetate. The combined ethyl acetate extracts are added to the aqueous filtrate and the resulting mixture shaken thoroughly for ten minutes. The phases are separated and the organic phase dried over magnesium sulfate. The drying agent is removed by filtration. The filtrate is evaporated to dryness in vacuo. The yellow solid is recrystallized from absolute ethanol to yield 33.7 g. (82%) of yellow needles melting at 189°-191°.

e. Ethyl (3-amino-2,4-dichloro-5-cyanophenyl)-oxamate

A solution of 32.3 g. (0.16 mole) of 2,4-dichloro-3,5-diaminobenzonitrile in 100 ml. of dimethyl-formamide, 250 ml. of ethyl acetate and 38.4 g. (0.38 mole) of triethylamine is cooled to 0° in an ice bath. To the solution is added 51.87 g. (0.38 mole) of ethyl oxalyl chloride and the temperature is kept below 18°. The reaction mixture is stirred in the ice-bath for 1 hour and allowed to warm to room temperature overnight.

The precipitate is removed by filtration. The filtrate is evaporated to dryness in vacuo. The oily residue is poured into 500 ml. of water, triturated, and the water decanted. The solid residue is boiled in 2 liters of ethanol. The insoluble material is removed by filtration. There is obtained 9.49 g. of a yellow solid that melts at 173°-175°. The filtrate is refrigerated and produces 25.5 g. of yellow needles that melt at 174°-175°.

Anal. Calcd. for: $C_{11}H_9Cl_2N_3O_3$ C, 43.73; H, 3.00; Cl, 23.47; N, 13.91. Found: C, 43.71; H, 3.03; Cl, 23.53; N, 14.01. Infrared: (Nujol mull) 3400, 3360, 3320, 3220 (NH), 2230 (C≡N), 1730 (C═O) 1625, 1575, 1520 (NH def./C═C) cm$^{-1}$. NMR: (DMSO-$D_6$) δ 10.33 (S, 1, NH), δ 7.50 (S, 1, aromatic), δ 6.22 (S, 2, $NH_2$), δ 4.33 (q. 2, $CH_2CH_3$), δ 1.32 (t, 2, $CH_2CH_3$).

f. (3-Amino-2,4-dichloro-5-cyanophenyl)-oxamic acid

A solution of 2.97 g. (0.01 mole) of ethyl (3-amino-2,4-dichloro-5-cyanophenyl)oxamate in 100 ml. of methylene chloride is placed in a separatory funnel. There is added a solution of 8 ml. of 1 N sodium hydroxide diluted to 100 ml. with water. There is added an additional 300 ml. of water to dissolve the sodium salt that forms. The phases are separated and the aqueous layer acidified with glacial acetic acid. To the solution is then added 5 ml. of concentrated hydrochloric acid. The precipitate is removed by filtration.

There is obtained 1.65 g. of yellow solid that melts at 212° (dec.). The solid is recrystallized from methanol. There is obtained 1.55 g. of colorless needles that melt at 213° (dec.).

Anal. Calcd. for: $C_9H_5Cl_2N_3O_3$ C, 39.44; H, 1.84; Cl, 25.87; N, 15.33. Found: C, 39.47; H, 1.93; Cl, 26.16; N, 15.48. U.V.: $\lambda_{max}$ 0.1 N NaOH 228 (ε=28,600), 329 (4,650) mμ NMR (DMSO-$D_6$): δ 10.21 (S, 1, NH), δ 7.53 (S, 1, aromatic), δ 6.22 (S, 2, $NH_2$).

EXAMPLE 15

In a similar manner to the preparation of the novel compounds of Examples 1 and 2, the following compounds are prepared:

| Compound | M.P.° C |
|---|---|
| Ethyl 3'-cyanooxanilate | 147–148 |
| 3'-cyano-oxanilic acid | 200 dec. |
| Methyl 4'-cyanooxanilate | 205–208 |
| 4'-cyano-oxanilic acid | 229 dec. |
| Ethyl 4'-chloro-3'-cyano-oxanilate | 184–185 |
| 4'-chloro-3-cyano-oxanilic acid | 206 dec. |
| Ethyl 3', 5'-dicyano-oxanilate | 190–193 |
| 3',5'-Dicyano-oxanilic acid | 233 dec. |
| Ethyl 3'-carboxyoxanilate | 218–222 |
| 3'-carboxyoxanilic acid | >320 |
| 1-ethyl-4'-nitro-3'-carboxy-oxanilate | 228–230 |
| 1-Ethyl-4'-amino-3'-carboxy-oxanilate | 225 |
| 1'-Ethyl-3'-carboxy-4'-hydroxy-oxanilate | 235–236 |
| Ethyl 4'-carboxy-3'-hydroxy-oxanilate | 255 dec. |
| Ethyl oxanilate | 65–66 |
| Oxanilic acid | 153–154 |

Some of the esters, for example, the benzyl and phenethyl, can have longer durations of activity.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of FIG. I. The preferred method of administration is by inhalation into the lung by means of an aerosol liquid or powder for insufflation.

For oral administration, either solid or fluid unit dosage forms can be prepared. For preparing solid compositions such as tablets, the compound of FIG. I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering a pH compatible with inhalation. The solutions are dispersed in a spray device or nebulizer and sprayed into the mouth while inhaling.

Aerosols are prepared by dispersing a compound of the FIG. I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form," as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.1 to about 50 mg. of compound in a single dose, administered parenterally or by inhalation in the compositions of this invention, are effective for preventing allergy attacks. More specifically, the single dose is from about 2.5 to about 25 mg. of compound. The oral and rectal dose is from about 10 to about 500 mg. in a single dose. More specifically, the single dose is from about 20 to about 250 mg. of compound. The dosage to be administered can be repeated up to four times daily.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 4

A lot of 10,000 tablets, each containing 100 mg. of (3-Amino-2,4-dichloro-5-cyanophenyl)-oxamic acid is prepared from the following types and amounts of ingredients:

| | |
|---|---|
| (3-Amino-2,4-dichloro-5-cyanophenyl)-oxamic acid | 1,000 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever or asthma attacks at a dose of one tablet every 6 hours.

EXAMPLE 5

One thousand tablets, each containing 50 mg. of (3-Amino-2,4-dichloro-5-cyanophenyl)oxamic acid are prepared from the following types and amounts of ingredients:

| | |
|---|---|
| (3-Amino-2,4-dichloro-5-cyanophenyl)-oxamic acid, | 50 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food-allergy at a dose of one tablet before meals.

EXAMPLE 6

A sterile preparation suitable for intramuscular injection and containing 10 mg. of (3-Amino-2,4-dichloro-5-cyanophenyl)oxamic acid in each milliliter is prepared from the following ingredients:

| | |
|---|---|
| (3-Amino-2,4-dichloro-5-cyanophenyl)oxamic acid | 10 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected to prophylactic treatment of allergic rhinitis.

EXAMPLE 7

Six hundred ml. of an aqueous solution containing 20 mg. of the THAM salt of (3-Amino-2,4-dichloro-5-cyanophenyl)oxamic acid per ml. is prepared as follows:

| | |
|---|---|
| THAM salt of (3-Amino-2,4-dichloro-5-cyanophenyl)oxamic acid | 12 Gm. |
| Sodium chloride | 5 Gm. |
| Water for injection q.s. | 600 ml. |

The compound of the above formulation and sodium chloride are dispersed in sufficient water to make 600 ml. and sterilized.

The liquid is placed in nebulizers designed to deliver 0.25 ml. per spray.

The liquid is inhaled into the lungs every 4 to 6 hours for prevention of asthmatic attacks.

EXAMPLE 8

A powder mixture consisting of 0.25 gram of the THAM salt of (3-Amino-2,4-dichloro-5-cyanophenyl)oxamic acid and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 9

A powder mixture consisting of 0.25 gram of (3-Amino-2,4-dichloro-5-cyanophenyl)oxamic acid and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 10

Twelve grams of an aerosol composition are prepared from the following ingredients:

| | |
|---|---|
| THAM salt of (3-Amino-2,4-dichloro-4-cyanophenyl)oxamic acid | 1.500 Gm. |
| Freon 12 | 1.440 Gm. |
| Freon 114 | 2,160 Gm. |
| Water | 6.300 Gm. |

| | |
|---|---|
| -continued | |
| Sorbitan monoleate | 0.600 Gm. |

The compound is dispersed in the water and chilled to −30° C. and added to the chilled Freons. The 12 grams of compositions are added to a 13 ml. plastic coated bottle and capped with a metering valve. The metering valve releases 80 mg. of composition in an aerosol. The aerosol is inhaled every 4 to 6 hours for prevention of asthmatic attacks.

EXAMPLE 11

After allowing for the differeing solubilities of the compounds and the activity of the particular compound as measured, for example, by the in vivo rat passive cutaneous anaphylaxis assay, a suitable quantity of each of the compounds of Table I through Table III and Example 1-3, is substituted for the active compound in the compositions and uses of Examples 3 through 10. Results showing anti-allergy activity are obtained.

EXAMPLE 12

The rat passive cutaneous anaphylaxis assay is run in the following manner:

Female Sprague-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. oval-bumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

It should be noted that in all the compositions and treatment examples of this patent application, the quantity of drug employed refers to the acid equivalent.

When repeated administration is desired, the compounds of this application which have a relatively short duration of activity can be administered in a priming dose-maintenance dose regimen as described in U.S. Ser. No. 382,762 at Page 58, line 19, to Page 59, line 9.

Following the procedure of Example 12 of this application, the inhibitory dose$_{50}$ of the THAM salt of (3-amino-2,4-dichloro-5-cyanophenyl)oxamic acid is 0.1 mg./kg. by the intravenous route.

I claim:

1. Compounds of the structure

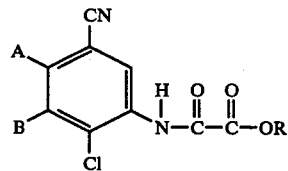

wherein A and B are both hydrogen or A is chloro and B is amino, and R is selected from the group consisting of hydrogen, a physiologically acceptable metal or amine cation, alkyl of one to six carbon atoms, inclusive, and phenyl.

2. A compound in accordance with claim 1 wherein A and B are hydrogen.

3. A compound in accordance with claim 1 wherein A is chloro and B is amino.

4. A compound in accordance with claim 2 wherein R is ethyl.

5. A compound in accordance with claim 3 wherein R is ethyl.

6. A compound in accordance with claim 2 wherein R is hydrogen or a physiologically acceptable metal or amine cation.

7. A compound in accordance with claim 3 wherein R is hydrogen or a physiologically acceptable metal or amine cation.

* * * * *